United States Patent [19]
Kasahara

[11] Patent Number: 5,282,782
[45] Date of Patent: Feb. 1, 1994

[54] VALGUS BIG TOE RECTIFYING SUPPORTER

[76] Inventor: Iwao Kasahara, 3734-6, Totsukacho, Totsuka-ku, Yokohama-shi, Kanagawa, Japan

[21] Appl. No.: 852,434

[22] Filed: Mar. 16, 1992

[30] Foreign Application Priority Data

Mar. 20, 1991 [JP]  Japan ................. 3-24794[U]
Feb. 19, 1992 [JP]  Japan ................. 4-69853

[51] Int. Cl.⁵ ............................................. A61F 5/00
[52] U.S. Cl. .................................... 602/30; 602/5
[58] Field of Search ............... 602/30, 5; 128/882, 128/892-894

[56] References Cited

U.S. PATENT DOCUMENTS

| | | | |
|---|---|---|---|
| 1,103,465 | 7/1914 | Arrowsmith | 602/30 |
| 1,497,151 | 6/1924 | Malkin | 602/30 |
| 1,785,185 | 12/1930 | Day | 602/30 |
| 2,190,016 | 2/1940 | Day et al. | 602/30 |
| 2,332,473 | 10/1973 | Salander | 602/30 |
| 2,416,823 | 3/1947 | Day | 602/30 |
| 2,596,038 | 5/1952 | Mayer | 602/30 |
| 3,049,120 | 8/1962 | Marcus | 602/30 |
| 4,632,103 | 12/1986 | Fabricant et al. | 602/30 |
| 4,637,381 | 1/1987 | Jungmann | 602/30 |
| 4,644,940 | 2/1987 | Nakamura | 128/882 X |

Primary Examiner—Stephen R. Crow
Assistant Examiner—Linda C. M. Dvorak
Attorney, Agent, or Firm—Jordan and Hamburg

[57] ABSTRACT

The present application is directed to a valgus big toe rectifying supporter which can prevent pain in and around a valgus big toe and its nail which will be caused by pressure exerted by the valgus toe or its nail, comprising a metatarsal joint securing band which will be firmly wound laterally around the metatarsal joint at the root of the big toe so that the metatarsal joint may be kept fastened, a big toe holding member which is connected to said metatarsal joint securing band and is attached to the big toe for holding the big toe in cooperation with said metatarsal joint securing band, a resilient member, for example, a sponge which is fixed integrally with or is separably attached to said big toe holding member and will be inserted between the big toe and the second toe, and a pulling band one end of which is connected to one side surface of said metatarsal joint securing band where said metatarsal joint securing band is integrated with said holding member and the other end of which can be wound around the heel of the foot through the inside surface of the foot and can be extended along the outer side surface of the foot to be connected to said metatarsal joint securing band.

6 Claims, 15 Drawing Sheets

VALGUS BIG TOE RECTIFYING SUPPORTER

FIELD OF THE INVENTION

The present invention relates to a supporter for rectifying a valgus big toe. More particularly, the present invention relates to a valgus big toe rectifying supporter for rectifying a valgus big toe which has been bent toward the second toe back to its normal state.

PRIOR ART

Figure 22:
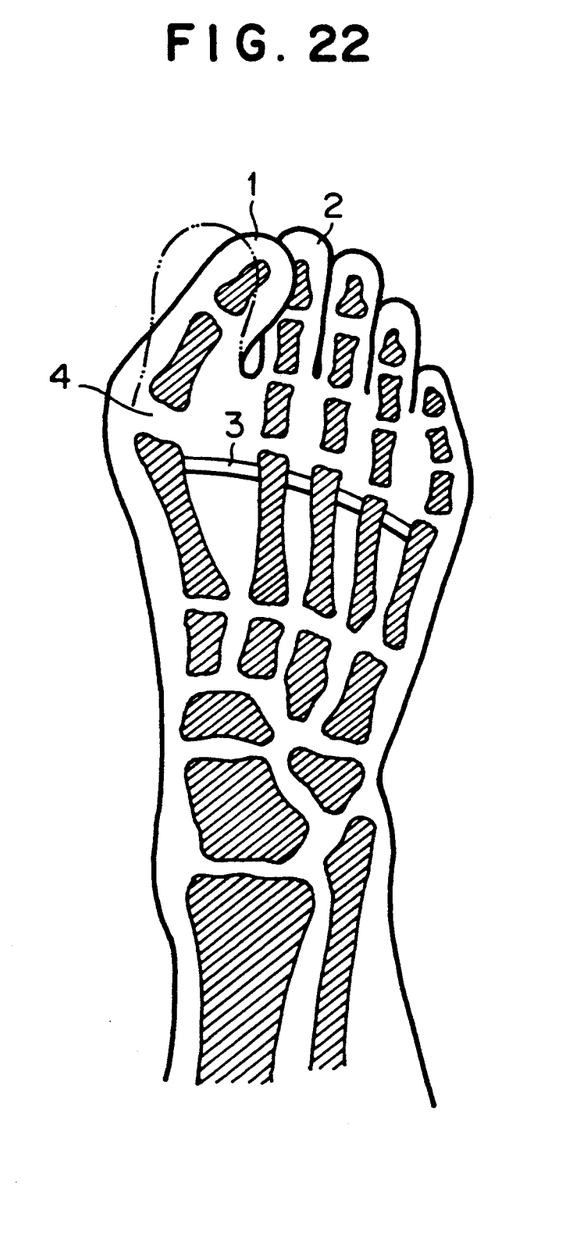
FIG. 22 is a view illustrating the skeleton of a valgus big toe.

As shown in FIG. 22, a valgus big toe is a deformed big toe 1 bent toward the second toe 2. This is caused when the transverse metatarsal band 3 has slackened, and particularly when the first metatarsal joint 4 has spread to cause the first toe 1 to be bent toward the second toe 2. The major cause which makes the big toe valgus is the fact that, these days, people seldom walk on the rugged ground and wear from their infant days shoes wherein they need not move their big toes, so that the toes are fixed. In particular, the toes are not required to move, thus lose the strength and gradually degenerate, so that it is considered that when one starts to run abruptly, the toe is pushed outward and bent. It is said that other cause is attributed to the fact that since people wear shoes with narrow toes they are liable to hurt the tips of their toes, the toes are tightened and the big toes are bent outward. When the is tightened and bent outward in this way, not only does one feel pain on the inside of the first metatarsal joint at the root of the big toe 1, but also the walking strength becomes weak, the balance of the parallel legs becomes unstable, and one is apt to fall and get hurt.

Figure 23:
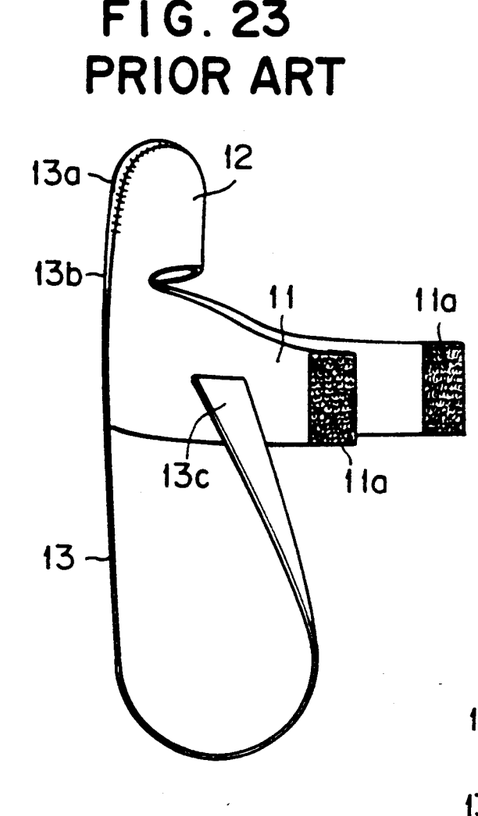
FIG. 23 is a plan view of a prior valgus big toe rectifying supporter.
Figure 24:
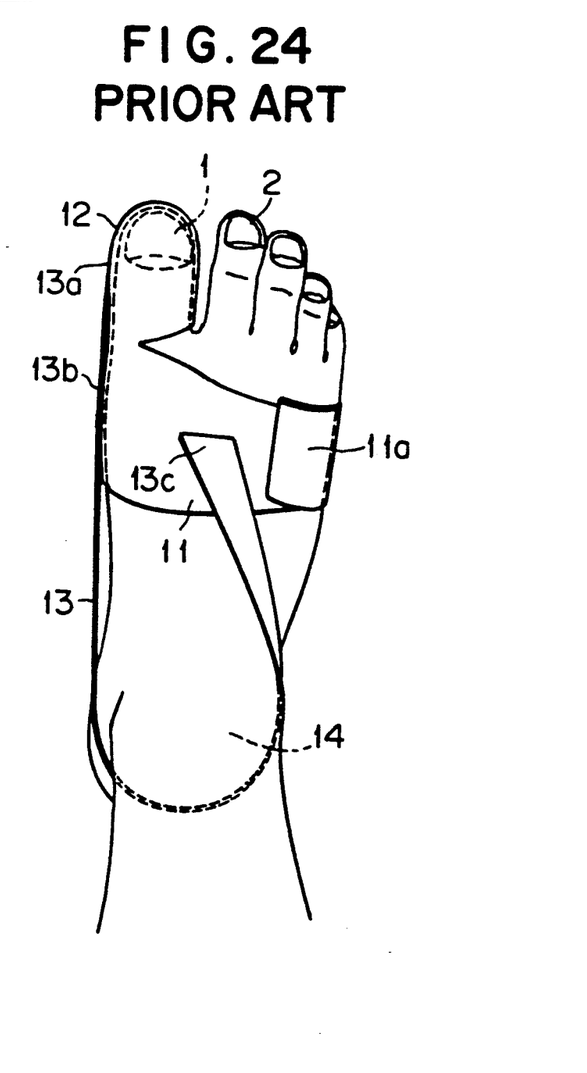
FIG. 24 is a plan view of the prior valgus big toe rectifying supporter which shows it in use.

To rectify the valgus big toe, the applicant suggested a valgus big toe rectifying supporter in Japanese Patent Publication 12094/1990 published on Mar. 19, 1990. The constitution of the valgus big toe rectifying supporter disclosed therein will now be described with reference to FIGS. 23 and 24. Reference numeral 11 indicates a cloth joint securing band for wrapping the first metatarsal joint together with other four metatarsophalangeal joints so that the first metatarsal section at the root of the big toe may be secured to its normal position. A velvet fastener is attached to almost all the outer surface of the joint securing band. Reference numeral 12 indicates a cloth big toe enclosing section connected to the joint securing band 11 which is capable of enclosing the big toe. Reference numeral 13 is a cloth pulling band which has an end 13a fixed to the outer side surface of the big toe enclosing section 12 and has a length which can extend from the end 13a along one outer side surface of the foot, then around the heel, and along the other outer side surface of the foot to the joint securing band 11. Velvet fasteners are attached to the pulling band 13 and the joint securing band 11 at parts where the pulling band 13 will abut on the joint securing band 11. When the valgus big toe rectifying supporter is applied, the big enclosing section is put on the big toe. The whole joints are wrapped in the joint securing band 11. The first metatarsal joint section at the root of the big toe is fastened so that the first metatarsal joint section may be in its normal position and a wrapping end 11a is fixed to the velvet fastener on the outer surface. Then, the pulling band 13 is pulled inward so that the valgus big toe may be returned back to its normal position, a section 13b is fixed by the joint securing band 11, the pulling band 13 is put around the heel 14, and the other end 13c is fixed to the joint securing band 11 at the most suitable position by the velvet fastener. However, although this valgus big toe supporter is effective for rectifying a valgus big the valgus big toe supporter has a defect that even though the valgus big toe is pulled to the inner normal position, the big toe and its nail cannot be prevented from being pressed and one feels pain caused around the big toe or its nail.

SUMMARY OF THE INVENTION

An object of the present invention is to provide a valgus big toe rectifying supporter which is effective for rectifying a valgus big toe and can prevent one from having pain in the valgus big toe or around its nail which will be caused by pressure on the valgus big toe or its nail.

The valgus big toe rectifying supporter according to the present invention comprises a metatarsal joint securing band which will be firmly wound around the metatarsal joint at the root of the big toe laterally of the foot so that the metatarsal joint may be kept fastened, a big toe holding member which is to be attached to the big toe and is integrally connected to said metatarsal joint securing band, a resilient member, for example, of a sponge which is fixed integrally to said big toe holding member and will be inserted between the big toe and the second toe, and a pulling band one end of which is connected to one side surface of said metatarsal joint securing band and the other end of which can be wound around the heel of the foot and can be extended along the outer side surface of the foot to be connected to said metatarsal joint securing band. By this constitution, the force of the valgus big toe which would otherwise be exerted on the second toe can be absorbed and weakened by the resilient member, so that a pain in the big toe and its nail can be mitigated and the deformed big toe can be rectified to its normal position.

DESCRIPTION OF THE PREFERRED EMBODIMENTS

Figure 1:
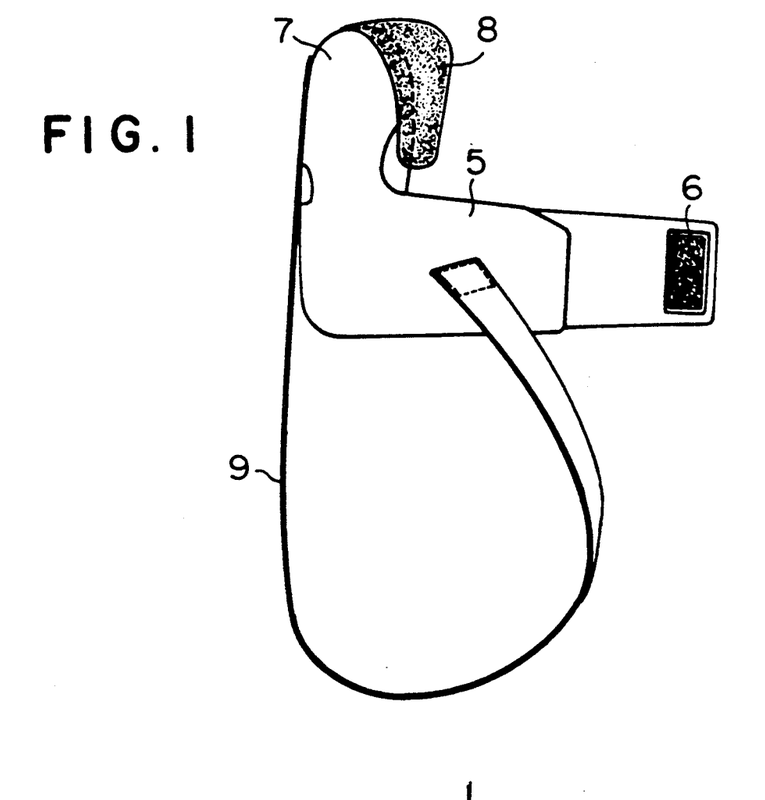
FIG. 1 is a front view of a first embodiment of the present invention.

A first embodiment of the present application will now be described with reference to FIGS. 1 to 3. A joint securing band 5 be wound laterally around the first metatarsal joint section 4 at the root of the big toe 1 to fasten and secure the first metatarsal joint section 4 to its normal position. A velvet fastener 6 is firmly attached to one end of the joint securing band 5. A big toe holding member 7 capable of enclosing the big toe 1 is connected to the upper edge of joint securing band 5. A resilient member 8, for example, a sponge, which is inserted between the big toe 1 an the second toe 2, is fixed to a side of said big toe holding member 7. A pulling band 9 has one end fixed to an outer side of the big toe holding member 7 and can extend along the inner side surface of the foot, around the heel, and along the outer side surface of the foot to reach the upper surface of the joint securing band 5. A velvet faster 10 is attached to the tip of the pulling band 9.

Figure 2:
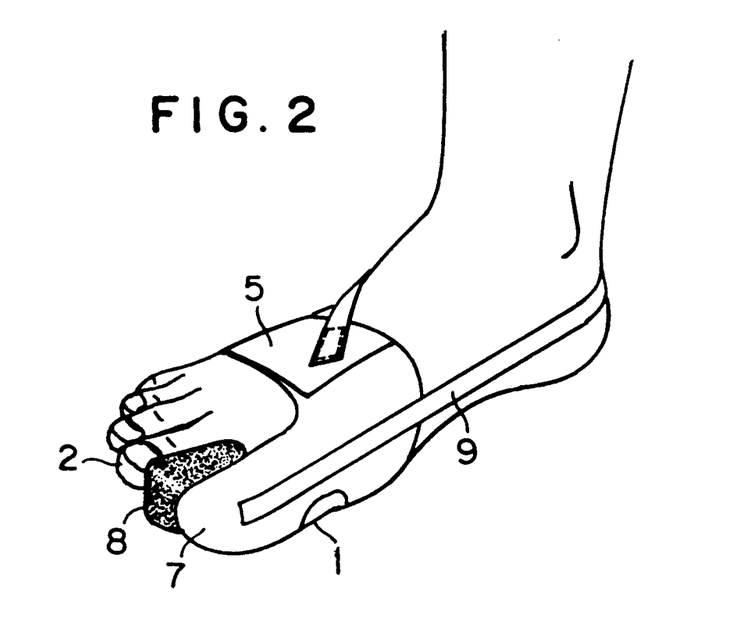
FIG. 2 is a perspective view of the embodiment of the present invention which shows it in use.
Figure 3:
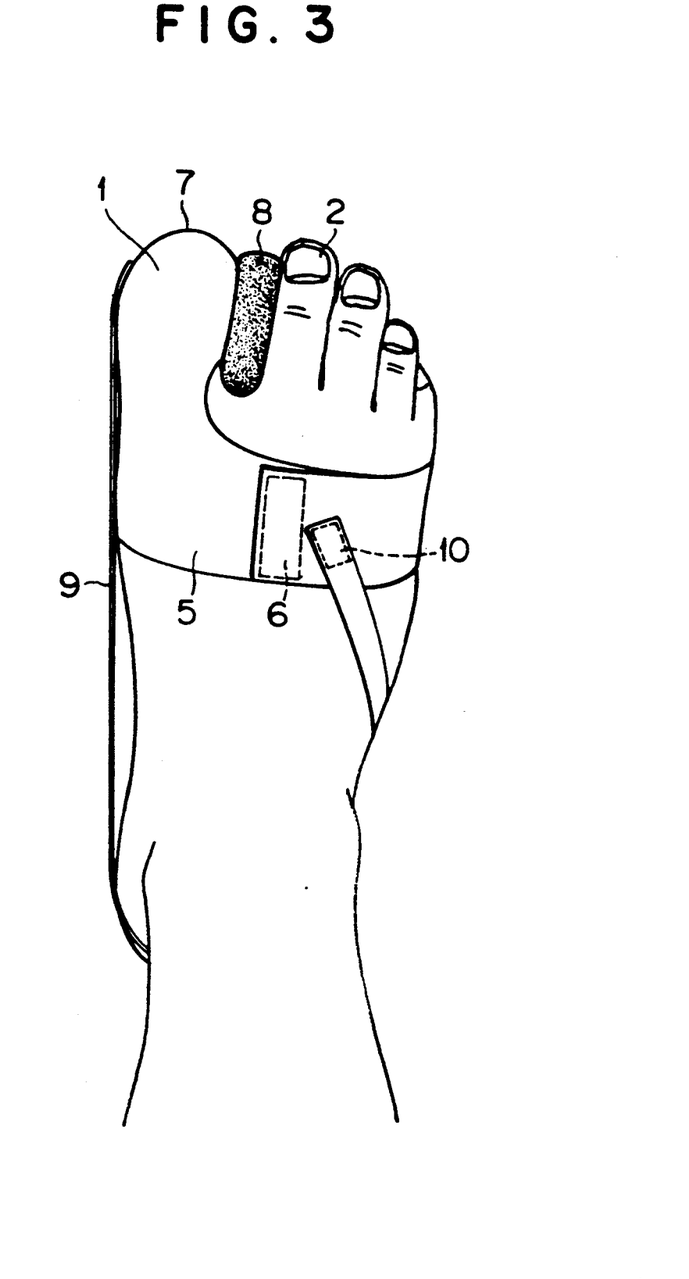
FIG. 3 is a top view of the first embodiment of the present invention which shows it in use.

When the supporter is to be used, as shown in FIGS. 2 and 3, first the big toe 1 is put in the big toe holding member 7 and at the same time the resilient member 8 is inserted between the big toe 1 and the second toe 2. Then, the first metatarsal joint section 4 at the root of the big toe 1 is pressed toward the little toe by the joint securing band 5 and with the whole metatarsal joint section 3 fastened the velvet fastener 6 is firmly attached to the other end of the joint securing band 5. Further, with the big toe 1 returned to its normal position the pulling band 9 is fixed to the inside of the joint securing band 5 and is turned around the heel, and the velvet fastener 10 at the end of the pulling band 9 is fixed to the upper surface of the joint securing band 5.

Figure 4:
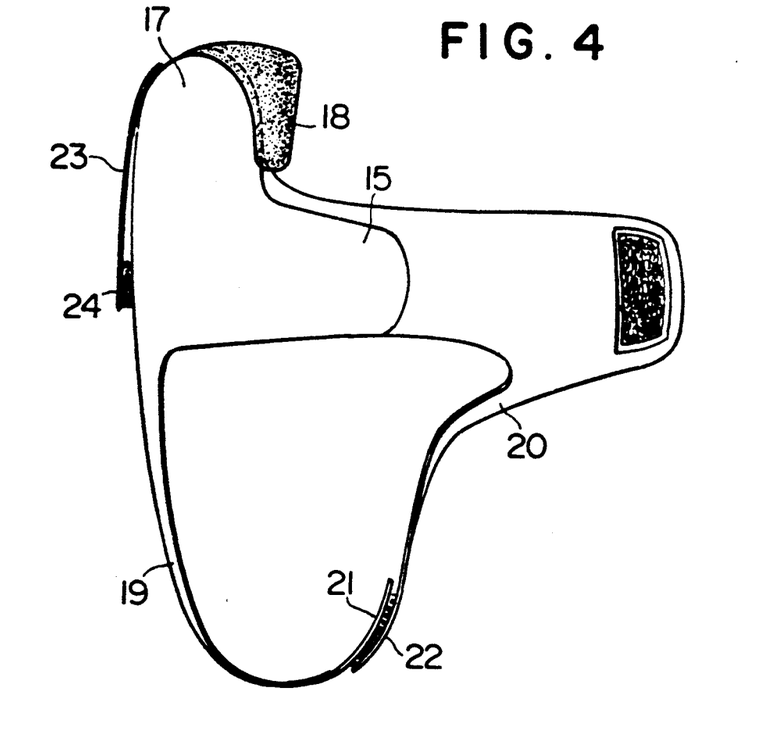
FIG. 4 is a front view of a second embodiment of the present invention.
Figure 5:
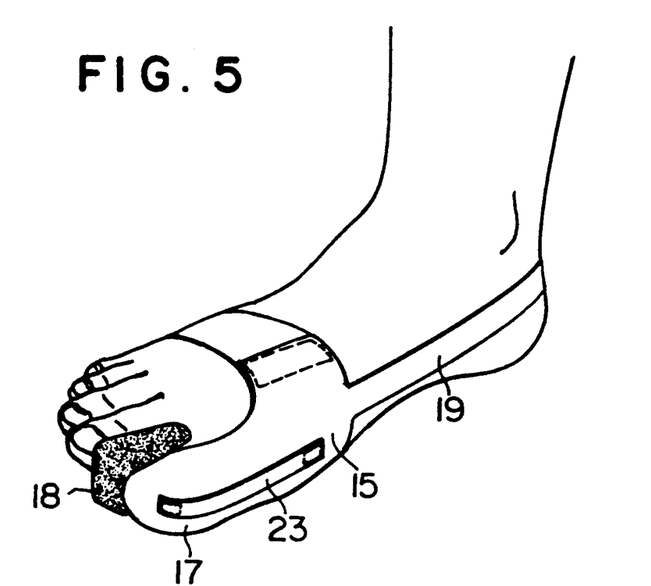
FIG. 5 is a perspective view of the second embodiment of the present invention which shows it in use.
Figure 6:
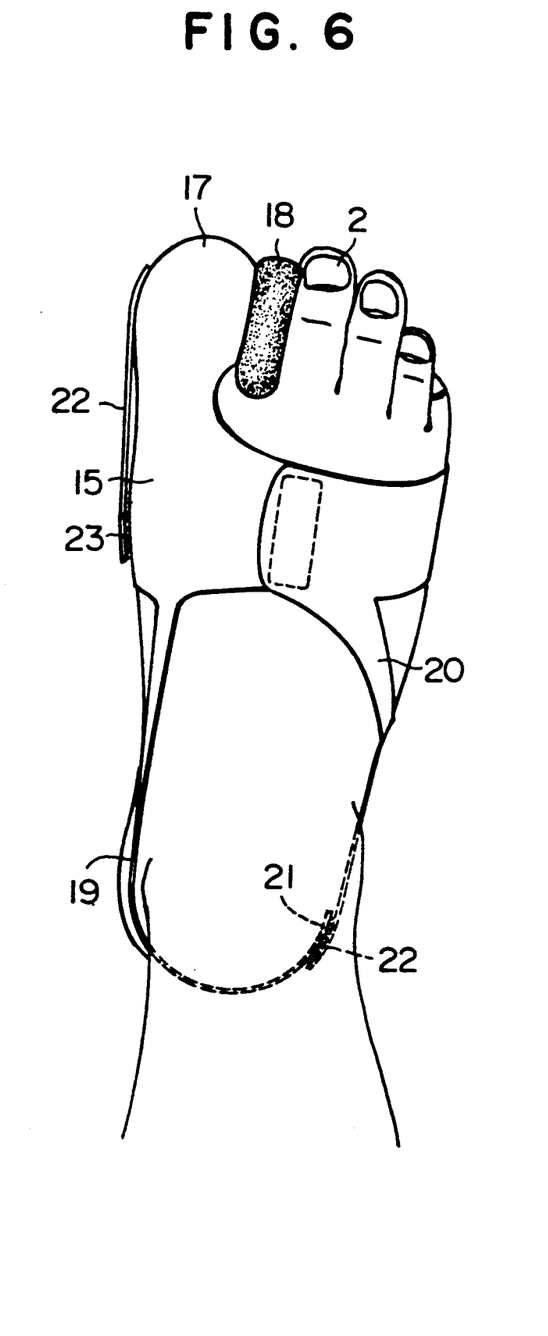
FIG. 6 is a top view of the second embodiment of the present invention which shows it in use.

A second embodiment of the present application will now be described with reference to FIGS. 4 to 6. A pulling band 19 which will be extended from one side of a metatarsal joint securing band 15 along the inner side surface of the foot to be turned around the heel is integrally formed with a pulling band 20 which will be extended from the other side of the metatarsal joint securing band 15 along the outer side surface of the foot and velvet fasteners 21 and 22 are fixed to the ends of the pulling bands 19 and 20 respectively. Reference numeral 17 indicates a big toe holding member capable of enclosing a big toe. A resilient member 18 for example, a sponge in the shape of a block which will be inserted between the big toe 1 and the second toe 2 is fixed to a side of said big toe holding member 17. One end of a big toe pulling band 23 is firmly attached to an outer surface of the big toe holding member 17 and the other end has a velvet fastener 24 fixed thereto. When the supporter is used, the big toe 1 is pulled inward to its normal position by the big toe pulling band 23 and the velvet fastener 24 is attached and fixed to the outer surface of the metatarsal joint securing band 15.

Figure 7:
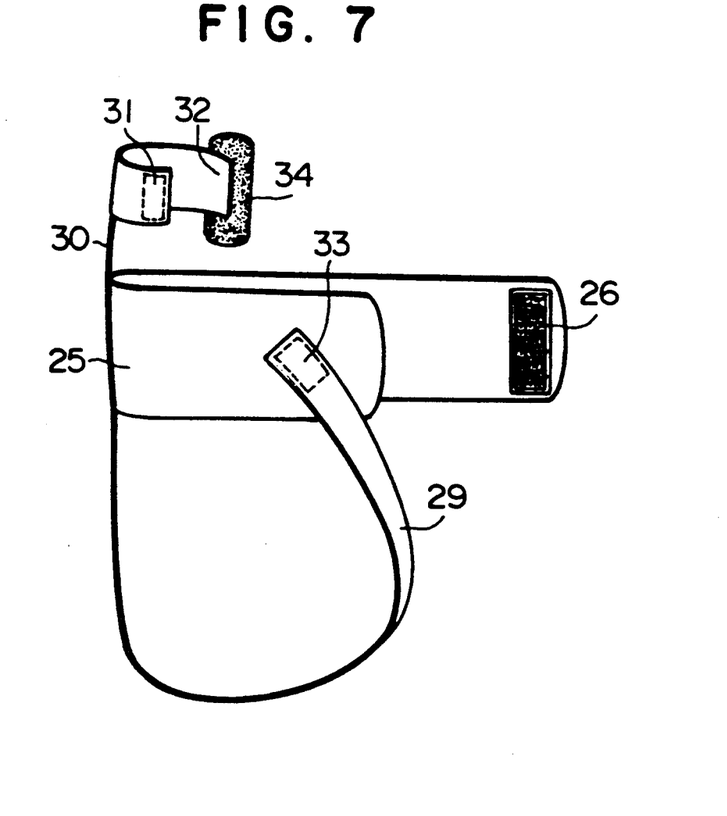
FIG. 7 is a front view of a t embodiment of the present invention.
Figure 8:
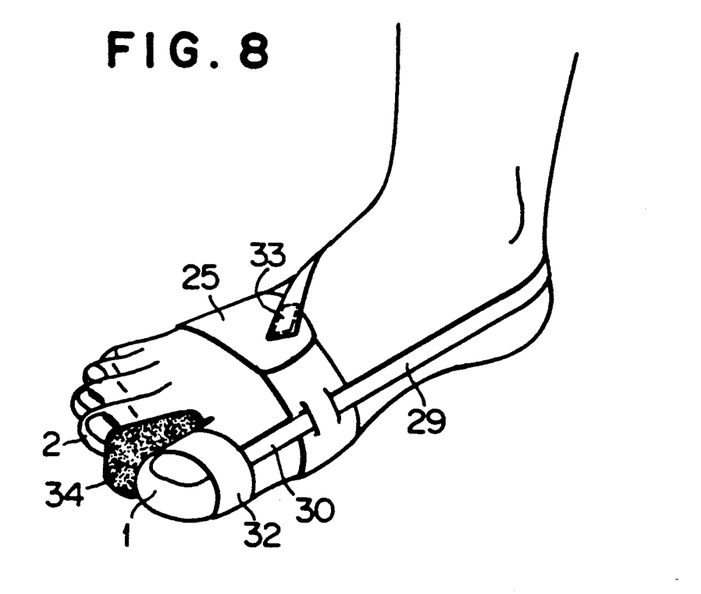
FIG. 8 is a perspective view of the third embodiment of the present invention which shows it in use.
Figure 9:
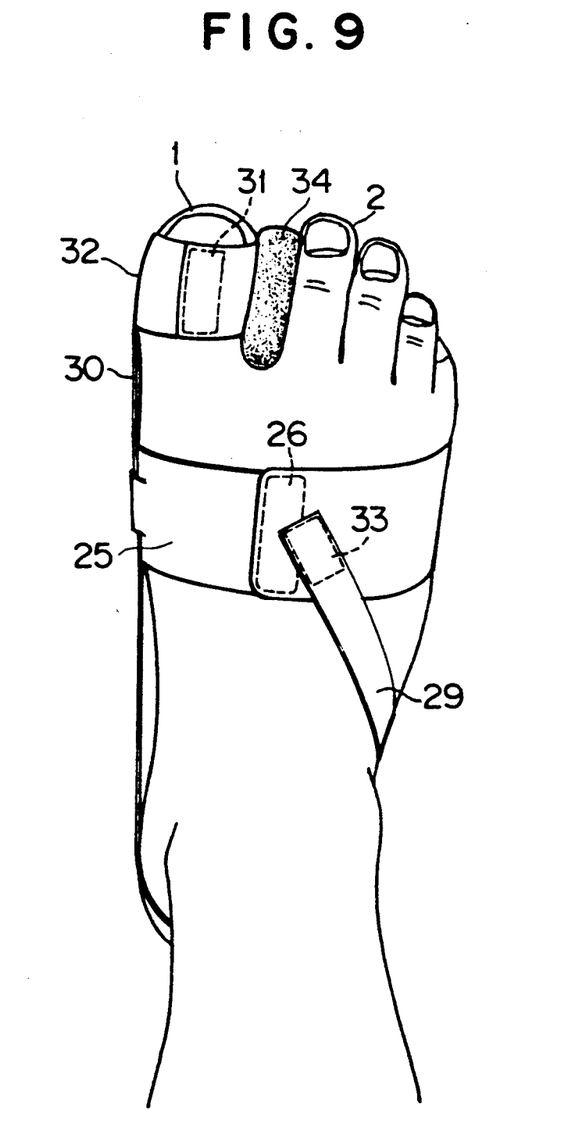
FIG. 9 is a top view of the third embodiment of the present invention which shows it in use.

A third embodiment of the present application will now be described with reference to FIGS. 7 to 9. A metatarsal joint securing member 25 will be wound laterally around the first metatarsal joint section 4 at the root of the big toe 1 so that it may be fastened and secured to its normal position, and a velvet fastener 26 is attached to an end of the metatarsal joint securing member 25. On one side of the metatarsal joint securing member 25, a pulling member 29 that has a length to be turned around the heel of the foot and to reach the metatarsal joint securing member 25 is connected or fixed to the metatarsal joint securing member 25 and an upper projection 30. A big toe holding member 32 that has a velvet faster 31 attached to its end and can be wound around the big toe to constitute a cylinder is fixed to the upper projection 30 where a pulling member 29 is connected or fixed to the other side of the metatarsal joint securing member 25. A velvet fastener 33 is attached to the other end of the pulling member 29 and will be fixed to the upper surface of the metatarsal joint securing member 25. A resilient member 34, for example, a sponge in the shape of a block which is inserted between the big toe 1 and the second toe 2 is fixed to one side of the big toe holding member 32.

Figure 10:
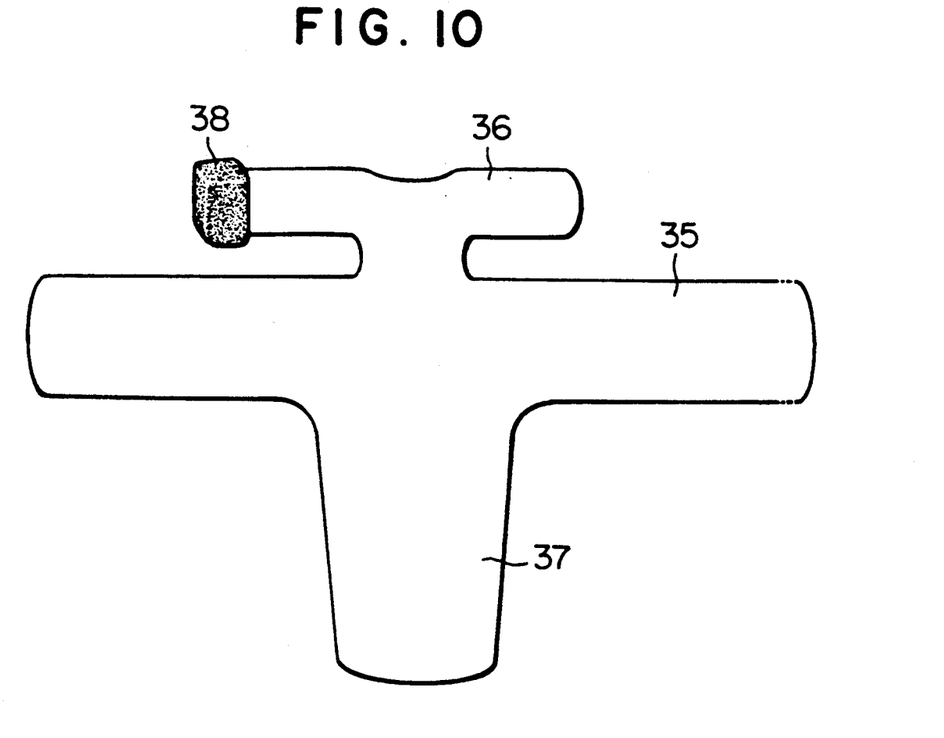
FIG. 10 is a front view of a embodiment of the present invention.
Figure 11:
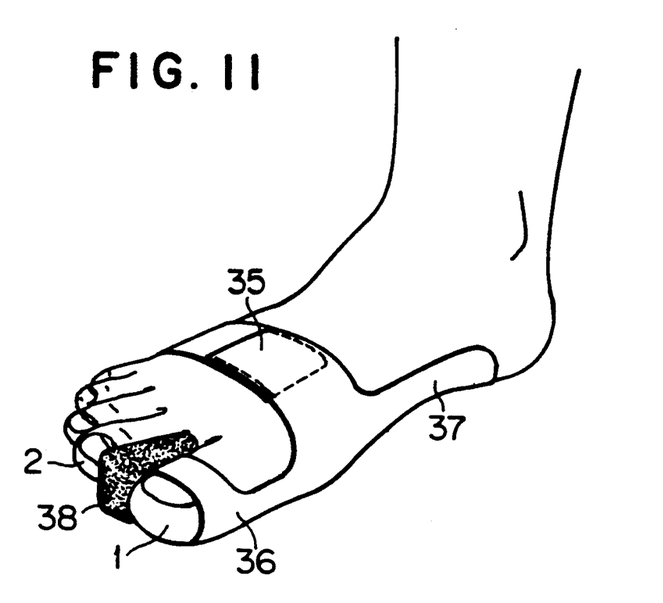
FIG. 11 is a perspective view of the fourth embodiment of the present invention which shows it in use.
Figure 12:
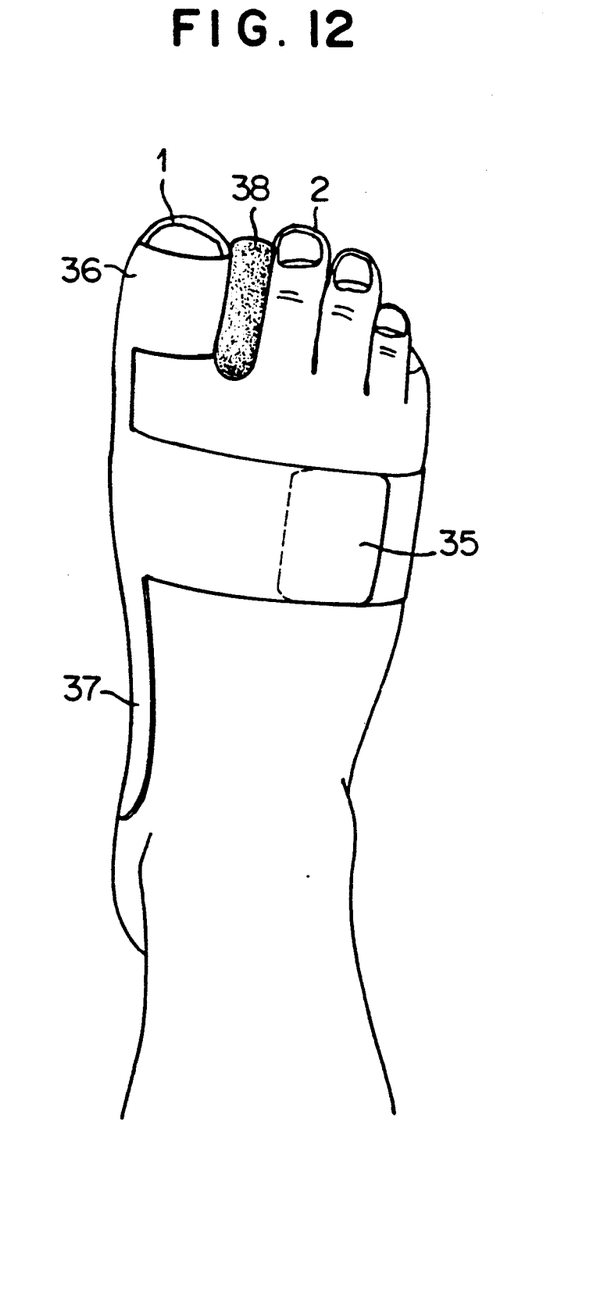
FIG. 12 is a top view of the, fourth embodiment of the present invention which shows it in use.

A fourth embodiment of the present application will now be described with reference to FIGS. 10 to 12. A metatarsal joint securing adhesive tape 35 will be wound laterally around the first metatarsal joint section 4 at the root of the big toe 1 so that the it may be kept fastened. A big toe holding adhesive tape 36 which is wound around the big toe 1 laterally is connected above the intermediate part of the metatarsal joint securing adhesive tape 35 and a foot side surface fitting adhesive tape 37 which will be stuck to the outer surface of the inside of the foot is longitudinally connected below the intermediate part. A resilient member 38, for example, a sponge that can be inserted between the big toe 1 and the second toe 2 is separably attached or stuck to one end of the big toe holding adhesive tape 36. On the surfaces of the adhesive tapes is stuck a release protective paper.

How to use it will now be explained with reference to FIGS. 11 and 12. First, the release protective paper is removed and the central part of the metatarsal joint securing adhesive tape 35 is stuck to the outer surface of the first metatarsal joint section 4 at the root of the big toe 1. Then, with the opposite sides of the joint securing adhesive tape 35 pulled toward each other, the joint securing adhesive tape 35 is stuck on the instep and the opposite sides thereof are stuck together. The resilient member 38 is inserted between the big toe 1 and the second toe 2 and the big toe holding adhesive tape 36 is wound around the big toe 1 laterally together with the resilient member 38 and is stuck thereto. Thereafter, the foot side surface fitting adhesive tape 37 is stuck and fixed to the outer surface of the inside of the foot and the heel.

Figure 13:
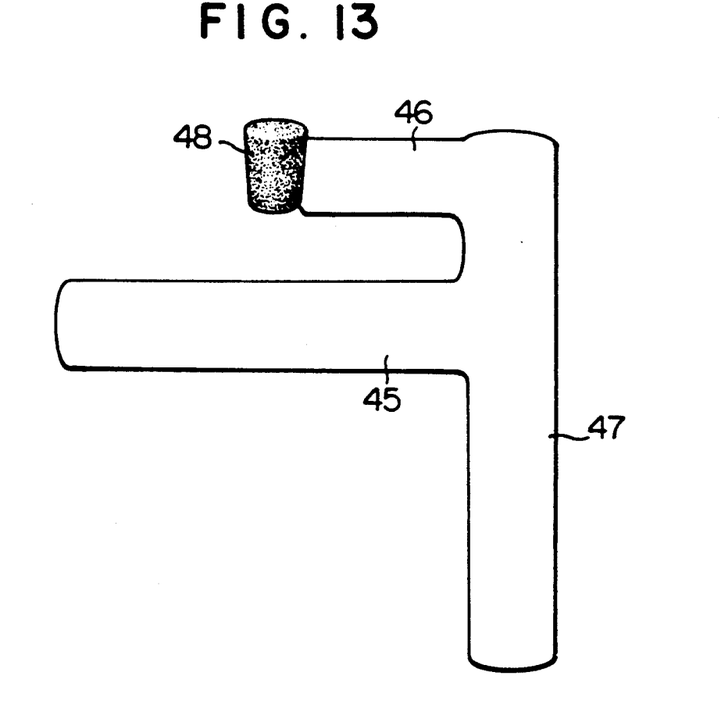
FIG. 13 is a front view of a fifth embodiment of the present invention.

FIG. 13 shows a fifth embodiment the present application. The difference the fifth embodiment the fourth embodiment is that a metatarsal joint securing adhesive tape 45 and a big toe holding adhesive tape 46 having a resilient member 48 separably attached or fixed at its end are provided on one side of a foot side fitting adhesive tape 47.

Figure 14:
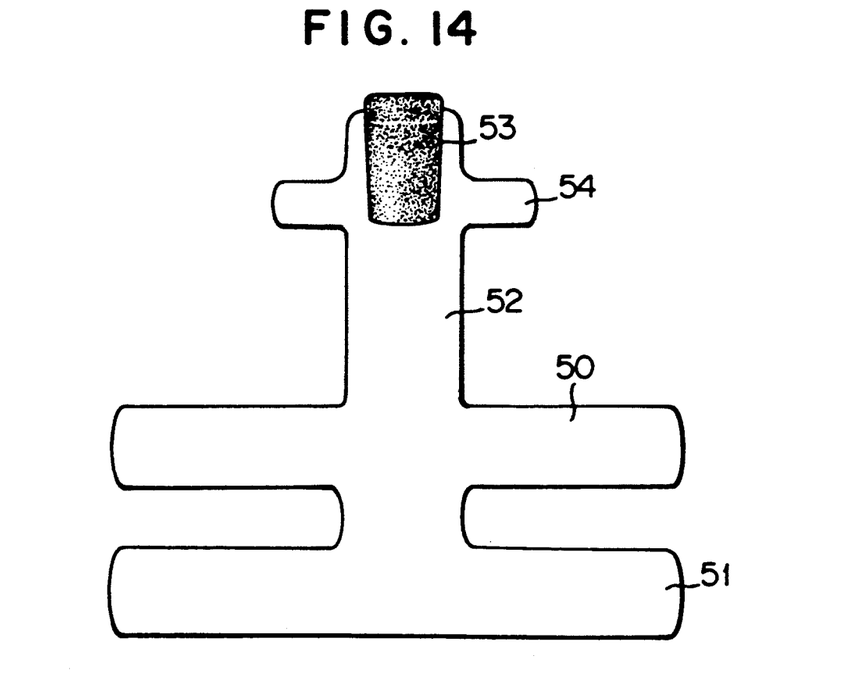
FIG. 14 is a front view of a sixth embodiment of the present invention.

A sixth embodiment of the present application will now be described with reference to FIGS. 14 to 15. Two metatarsal securing adhesive tapes 50 and 51 will be wound laterally around the metatarsophalangeal joint 4 at the root of the big toe 1 so that it may be kept fastened. The metatarsal joint securing adhesive tape 50 and 51 are arranged in parallel and are connected at their central parts. Above the central parts of the metatarsal joint securing adhesive tapes 50 and 51 are connected a longitudinal big toe holding adhesive tape 52 which will be wound around the big toe 1 longitudinally and a lateral big toe holding adhesive tape 54 which will be wound around the big toe laterally. A resilient member 53, for example, a sponge is separably attached or fixed to the upper part of the longitudinal big toe holding adhesive tape 52. Instead of the two metatarsal joint securing adhesive tapes 50 and 51, only one metatarsal joint securing adhesive tape may be used.

Figure 15:
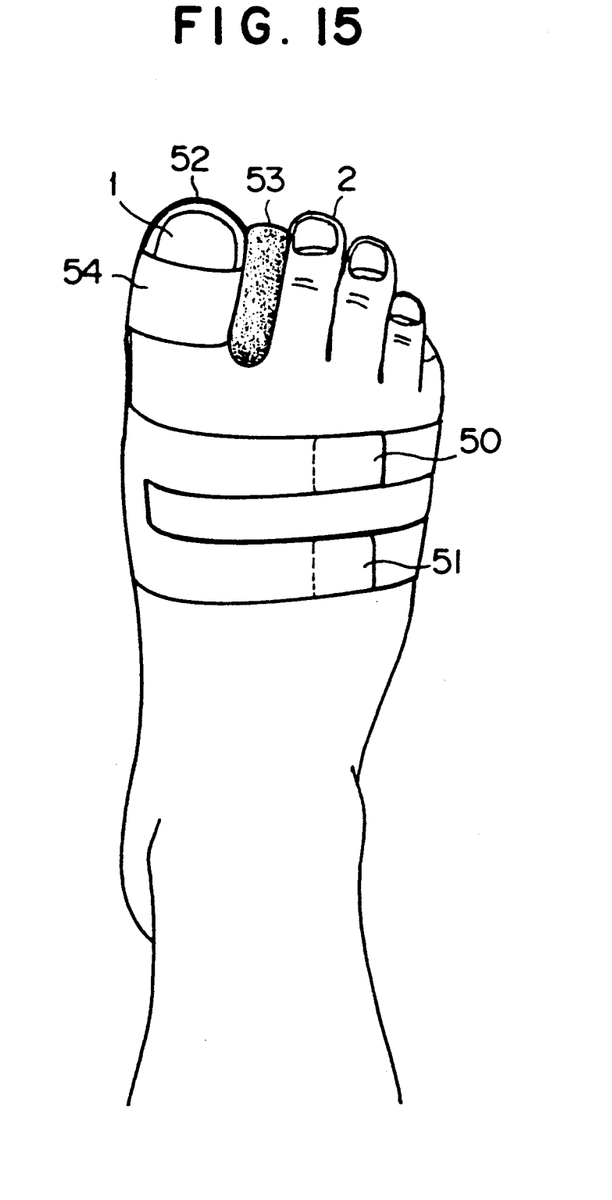
FIG. 15 is a top view of the sixth embodiment of the present invention which shows it in use.
Figure 16:
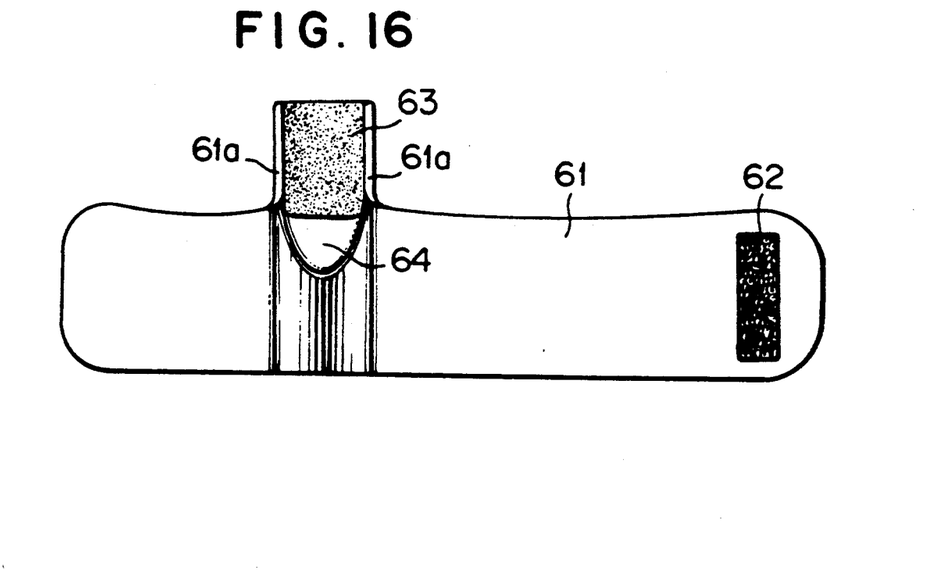
FIG. 16 is a bottom view of a seventh embodiment of the present invention in its open state.
Figure 17:
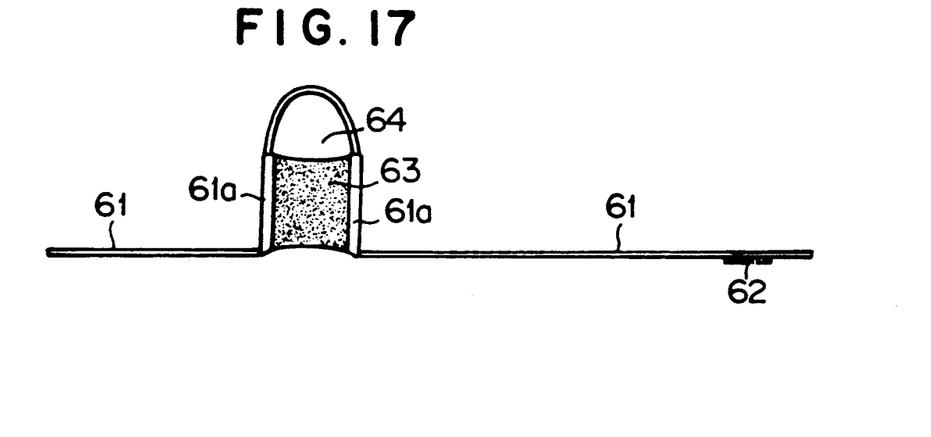
FIG. 17 is a side view of the seventh embodiment of the present invention in its open state.
Figure 18:
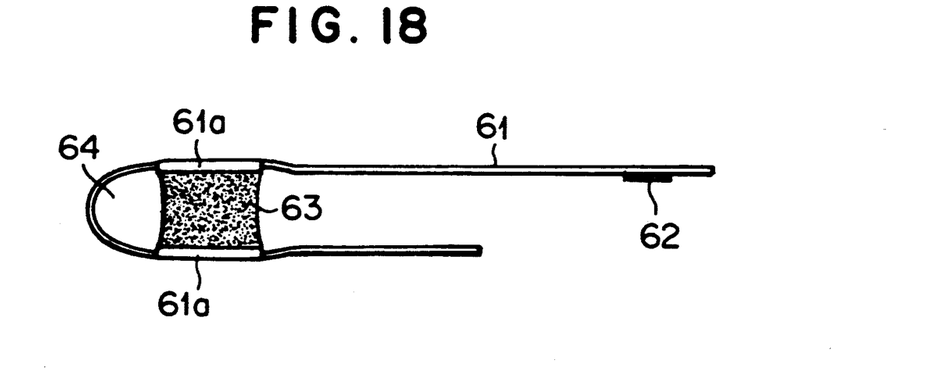
FIG. 18 is a side view of the seventh embodiment of the present invention, similar to FIG. 17, except the left hand portion has been rotated 90° in a counter-clockwise direction.

FIG. 15 shows the sixth embodiment in use. The release protective paper on the adhesive tape is removed and the longitudinal big toe holding adhesive tape 52 is wound around the big toe 1 longitudinally. The resilient member 53 is inserted between the big toe 1 and the second toe 2 and the lateral big toe holding adhesive tape 54 is wound around the big toe 1 laterally and is stuck thereto. Then the metatarsal joint securing adhesive tapes 50 and 51 are stuck to the outer surface of the first metatarsal joint section 4 at the root of the big toe 1. Further, the metatarsal joint securing adhesive tapes 50 and 51 are fastened to the whole metatarsal joint 3 with the foot laterally pressed and the opposite ends thereof are stuck and fixed to the instep and then are stuck together. The resilient member 53 may be separated and when it is used, the resilient member 53 is inserted between the big toe 1 and the second toe 2 and may be fixed by winding the longitudinal big toe holding adhesive tape 52 and the lateral big toe holding adhesive tape 54.

A seventh embodiment of the present application will now be described with reference to FIGS. 16 to 21. A metatarsal joint securing band 61 will be wound around the section of the metatarsophalangeal joint 4 of the big toe 1 laterally so that it may be kept fastened. A velvet fastener 62 is stuck to an end of the metatarsal joint securing band 61. A pair of projection pieces 61a and 61a are projected from the upper edge of the metatarsal joint securing band 61 and the opposite sides of a resilient member 63, for example, of a sponge, which is inserted between the big toe 1 and the second toe 2, are attached firmly to the projection pieces 61a and 61a. An opening 64 from which the big toe 1 will project is formed in the upper edge of the metatarsal joint securing band 61 and is situated below the resilient member 63.

Figure 19:
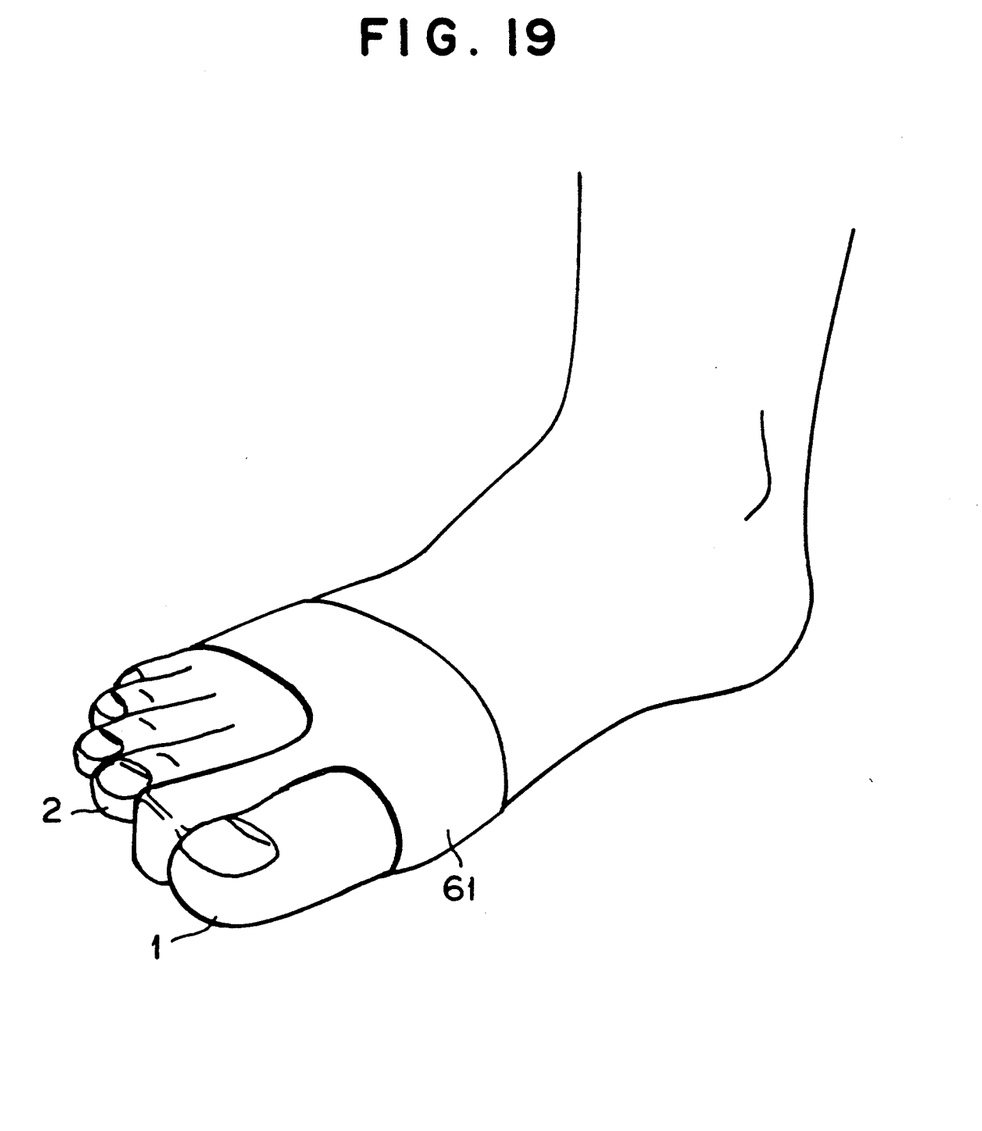
FIG. 19 is a perspective view of the seventh embodiment of the present invention which shows it in use.
Figure 20:
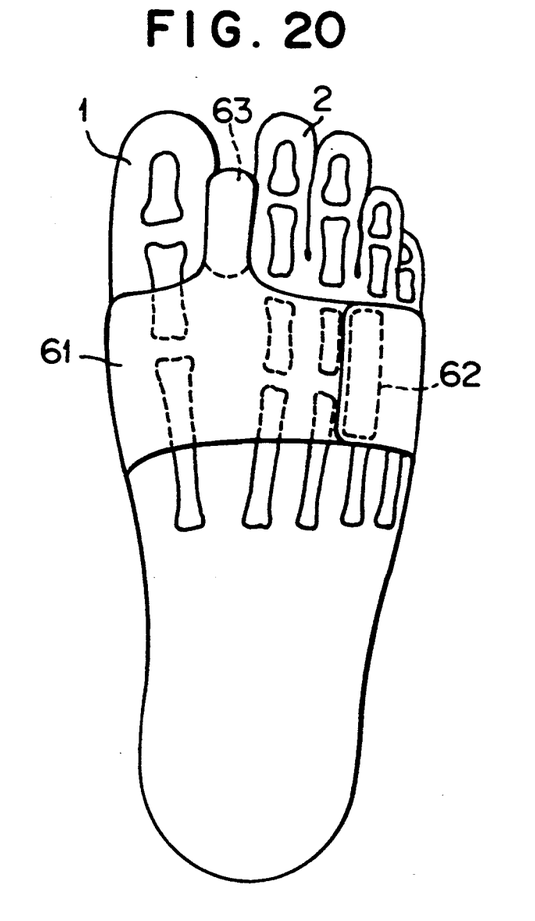
FIG. 20 is a top view of the seventh embodiment of the present invention which shows it in use.
Figure 21:
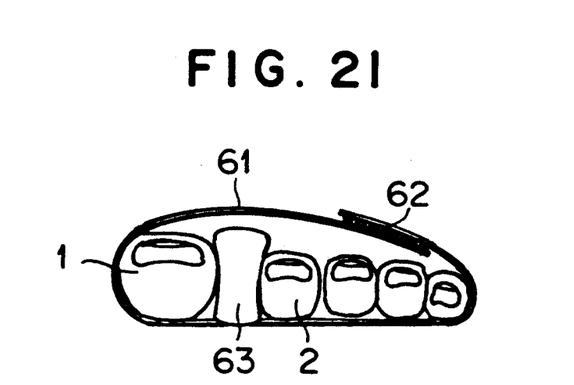
FIG. 21 is a front view of the seventh embodiment of the present invention which shows it in use.

How to use it will now be explained with reference to FIGS. 19 and 21. First, the big toe 1 is put in and projected upward into the opening 64 and at the same time the resilient member 63 is inserted between the big toe 1 and the second toe 2. Then, the section of the first metatarsophalangeal joint 4 at the big toe 1 is pulled toward the little toe by the metatarsal joint securing band 61 with the first metatarsophalangeal joint 4 fastened in this way, the velvet fastener 62 is firmly attached to the other end of the metatarsal joint securing band 61. In the metatarsal joint securing band 61, an adhesive may be applied to all the undersurface of the plastic sheet constituting the metatarsal joint securing band 61 and a release paper may be stuck to the adhesive, and when it is used the release paper is removed and the plastic sheet may be stuck firmly directly to the foot. The projection pieces 61a on the metatarsal joint securing band 61 may be omitted and the lower part of the resilient member 63 may be firmly attached directly to the upper edge of the metatarsal joint securing band 61.

What is claimed is:

1. A valgus big toe rectifying supporter comprising:
(a) a metatarsal joint securing band adapted to be disposed in a fitted disposition in which the band is wound on a foot at a metatarsal joint, said band having a forward edge and a rear edge, said forward edge extending around the foot at the forward portion of the matatarsal joint, said rear edge extending around the foot at the rear portion of the metatarsal joint, said forward edge being adapted to be spaced from the second, third, fourth and fifth toes, said band having an inside part adapted to be juxtaposed to the inside of the foot and an outside part adapted to be juxtaposed to the outside of the foot;
(b) a big toe holder extending forwardly from said forward edge at the inside part of said band, said holder having a forward section and a rear section, said rear section being integrally joined with said band at the forward edge of the inside part of said band;
(c) said forward section of said holder being formed as an enclosure which extends around the front, the sides, the top and the bottom of the big toe to completely enclose the front part of the big toe;
(d) said forward section of said holder having a top portion extending over the top of the big toe, said rear section of said holder having a top portion extending over the top of the big toe and which forms an integral continuation of said top portion of said forward section of said holder, said top portion of said rear section of said holder being narrower than said top portion of said forward section of said holder;
(e) said forward section of said holder having an inside portion extending between the big toe and the second toe;
(f) a resilient member, connecting means integrally connecting said resilient member to said inside portion of said forward section of said holder, said resilient member being adapted to be disposed between the big toe and the second toe;
(g) said inside portion of said forward section of said holder having a rear terminating edge which is spaced from said front edge of said band and which is also adapted to be disposed forwardly of the juncture where the big toe joins the second toe to thereby define an opening which exposes the inside rear portion of the big toe;
(h) said resilient member having a length sufficient to extend the length of the big toe from the tip of the big toe to the juncture where the big toe meets the second toe;

(i) said resilient member having a forward part which is connected to said inside portion of said forward section of said holder by said connecting means, said resilient member having a rear part which is adapted to extend rearwardly substantially to the juncture where the big toe joins the second toe and which extends along side said opening and is adapted to directly engage the inside rear portion of the big toe; and (j) a pulling strap extending from said band and which is adapted to be wound around a heel of the foot from an inside surface of the foot to an outside surface of the foot.

2. A valgus big toe rectifying supporter according to claim 1 wherein said resilient member in its natural unflexed state is tapered with said forward part being wider than said rear part.

3. A valgus big toe rectifying supporter according to claim 1 wherein said band has a pre-fitted disposition prior to disposing the band in said fitted disposition on a foot wherein a generally flat upper band part overlies a generally flat lower band part and wherein each of said upper and lower band parts have one end portion which are integrally joined to one another and each of said upper and lower band parts having a terminating end portion, said upper band portion progressively narrowing from its one end portion to its terminating end portion, said lower band portion progressively narrowing from its one end portion to its terminating end portion.

4. A valgus big toe rectifying supporter according to claim 1 wherein said forward section of said holder has a side part adapted to be juxtaposed to the outer side of the big toe, said band having a side part positioned at the inside of the foot juxtaposed to the metararsal joint, an auxiliary pulling member having a forward end part and a rear end part, forward attaching means attaching said forward end part of said pulling member to said side part of said forward section of said holder, and detachable attaching means detachably attaching said rear end part of said pulling member to said side part of said band, whereby said auxiliary pulling member is adjustable by said detachable attaching means to adjust the extent of rearward pull of said pulling member on said holder.

5. A valgus big toe rectifying supporter according to claim 4 wherein said pulling strap has two ends, said band and said pulling strap being integrally formed from a single piece of material such that one end of the pulling strap extends integrally from one section of said rear edge of said band and the other end of the pulling strap extends integrally from another section of said rear edge of said band.

6. A valgus big toe rectifying supporter comprising:

(a) a metatarsal joint securing band adapted to be disposed in a fitted disposition in which the band is wound on a foot at a metatarsal joint, said band having a forward edge and a rear edge, said forward edge extending around the foot at the forward portion of the metatarsal joint, said rear edge extending around the foot at the rear portion of the metatarsal joint, said forward edge being adapted to be spaced from the second, third, fourth and fifth toes, said band having an inside part adapted to be juxtaposed to the inside of the foot and an outside part adapted to be juxtaposed to the outside of the foot;

(b) a big toe holder extending forwardly from said forward edge at the inside part of said band, said holder having a forward section and a rear section, said rear section being integrally joined with said band at the forward edge of the inside part of said band;

(c) said forward section of said holder being formed as an enclosure which extends around the front toe sides, toe top and the bottom of the big toe to completely enclose the front part of the big toe;

(d) said forward section of said holder having a top portion extending over the top of the big toe, said rear section of said holder having a top portion extending over the top of the big toe and which forms an integral continuation of said top portion of said forward section of said holder, said top portion of said rear section of said holder being narrower than said top portion of said forward section of said holder;

(e) said forward section of said holder having an inside portion extending between the big toe and the second toe;

(f) a resilient member, connecting means integrally connecting said resilient member to said inside portion of said forward section of said holder, said resilient member being adapted to be disposed between the big toe and the second toe, said resilient member in its natural and unflexed state being tapered with its forward part being wider than its rear part;

(g) said inside portion of said forward section of said holder having a rear terminating edge which is spaced from said front edge of said band and which is also adapted to be disposed forwardly of the juncture where the big toe joins the second toe to thereby define an opening which exposes the inside rear portion of the big toe;

(h) said resilient member having a length sufficient to extend the length of the big toe from the tip of the big toe to the juncture where the big toe meets the second toe;

(i) said resilient member having a forward part which is connected to said inside portion of said forward section of said holder by said connecting means, said resilient member having a rear part which is adapted to extend substantially to the juncture where the big toe joins the second toe and which extends along side said opening and is adapted to directly engage the inside rear portion of the big toe; and (j) a pulling strap extending from said band and which is adapted to be wound around a heel of the foot from an inside surface of the foot to an outside surface of the foot.

(k) said band having a pre-fitted disposition prior to disposing the band in said fitted disposition on a foot wherein a generally flat upper band part overlies a generally flat lower band part and wherein each of said upper and lower band parts have one end portion which are integrally joined to one another and each of said upper and lower band parts having a terminating end portion, said upper band portion progressively narrowing from its one end portion to its terminating end portion, said lower band portion progressively narrowing from its one end portion to its terminating end portion.

* * * * *